United States Patent
Hatanaka et al.

(10) Patent No.: US 9,625,386 B2
(45) Date of Patent: Apr. 18, 2017

(54) IMAGING SYSTEM

(71) Applicants: IWASAKI ELECTRIC CO., LTD., Tokyo (JP); KOCHI UNIVERSITY, Kochi-shi (JP)

(72) Inventors: Mitsuyuki Hatanaka, Gyoda (JP); Takashi Sato, Gyoda (JP); Nozomu Kajiwara, Gyoda (JP); Takaaki Komiya, Gyoda (JP); Takayuki Sato, Kochi (JP)

(73) Assignees: IWASAKI ELECTRIC CO., LTD., Tokyo (JP); KOCHI UNIVERSITY, Kochi-Shi (JP)

( * ) Notice: Subject to any disclaimer, the term of this patent is extended or adjusted under 35 U.S.C. 154(b) by 0 days.

(21) Appl. No.: 14/482,614

(22) Filed: Sep. 10, 2014

(65) Prior Publication Data

US 2016/0069807 A1 Mar. 10, 2016

(51) Int. Cl.
| | |
|---|---|
| *G01N 21/359* | (2014.01) |
| *G01N 21/64* | (2006.01) |
| *A61B 5/00* | (2006.01) |

(52) U.S. Cl.
CPC ....... *G01N 21/6456* (2013.01); *A61B 5/0071* (2013.01); *G01N 21/359* (2013.01);
(Continued)

(58) Field of Classification Search
CPC ..... G01N 21/6486; G01N 2201/06113; G01N 21/64; G01N 21/6458
See application file for complete search history.

(56) References Cited

U.S. PATENT DOCUMENTS

| | | |
|---|---|---|
| 2002/0044212 A1 | 4/2002 | Hashimoto |
| 2005/0253087 A1 | 11/2005 | Plan |
| | (Continued) | |

FOREIGN PATENT DOCUMENTS

| | | |
|---|---|---|
| DE | 10157575 A | 4/2003 |
| DE | 102009025662 A | 12/2010 |
| | (Continued) | |

OTHER PUBLICATIONS

Office Action mailed Jun. 8, 2015 for the corresponding German Application No. 102014218202.6.
(Continued)

*Primary Examiner* — Christine Sung
(74) *Attorney, Agent, or Firm* — Leason Ellis LLP

(57) ABSTRACT

An imaging system includes: a first lighting device for irradiating an imaging target object with visible light; a second lighting device for irradiating the imaging target object with near-infrared light; and an image sensor for photodetecting visible light caused by the visible light and coming from the imaging target object and fluorescence caused by the near-infrared light and coming from the imaging target object during a predetermined shutter open period every frame of a predetermined period. The image sensor outputs photodetection signals corresponding to photodetection amounts of the visible light and the fluorescence. The imaging system also includes a controller that generates a composite image of a visible image and a fluorescence image based on the photodetection signals, and has a lighting controller that turns on the second lighting device with optical power corresponding to the shutter open period in synchronism with the shutter open period.

13 Claims, 9 Drawing Sheets

(52) U.S. Cl.
CPC ..... G01N 21/6408 (2013.01); G01N 21/6486 (2013.01); *G01N 2021/646* (2013.01); *G01N 2201/061* (2013.01); *G01N 2201/0621* (2013.01); *G01N 2201/0696* (2013.01)

(56) References Cited

U.S. PATENT DOCUMENTS

| | | | |
|---|---|---|---|
| 2009/0065679 A1 | 3/2009 | Tanimoto | |
| 2009/0203994 A1* | 8/2009 | Mangat | A61B 5/0261 600/433 |
| 2009/0285762 A1* | 11/2009 | Flower | A61K 47/48776 424/9.6 |
| 2009/0289200 A1 | 11/2009 | Ishii | |
| 2010/0322492 A1 | 12/2010 | Stepp et al. | |
| 2013/0096376 A1* | 4/2013 | Takei | G02B 23/2461 600/103 |
| 2015/0018690 A1* | 1/2015 | Kang | A61B 5/418 600/473 |
| 2015/0025391 A1* | 1/2015 | Mackie | A61B 5/0071 600/476 |

FOREIGN PATENT DOCUMENTS

| | | |
|---|---|---|
| JP | 10-151104 A | 6/1998 |
| JP | 2002-189238 A | 7/2002 |
| JP | 2004-205557 A | 7/2004 |
| JP | 2008-188196 A | 8/2008 |
| JP | 2009-066121 A | 4/2009 |
| JP | 2009-279171 A | 12/2009 |
| JP | 2011-206227 A | 10/2011 |
| WO | WO 2011/007461 A1 | 1/2011 |

OTHER PUBLICATIONS

International Search Report mailed Dec. 22, 2009 for the related PCT Application No. PCT/JP2009/067352.
Office Action mailed Jan. 10, 2017 for the corresponding Japanese Patent Application No. 2013-105130.

* cited by examiner

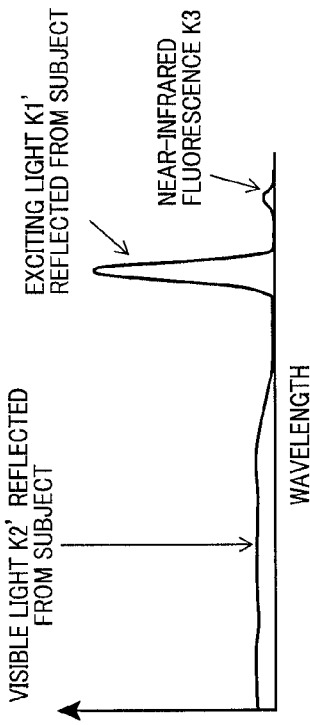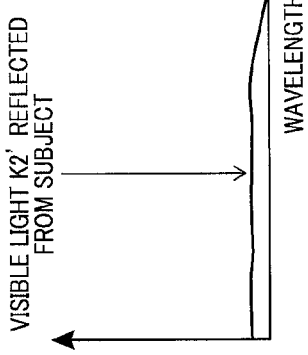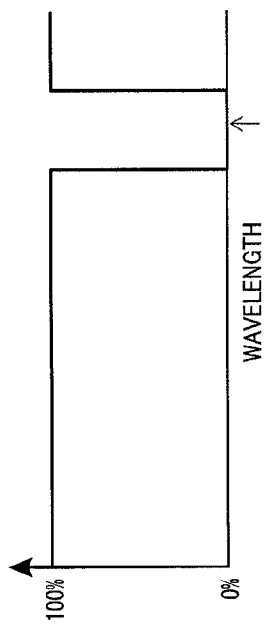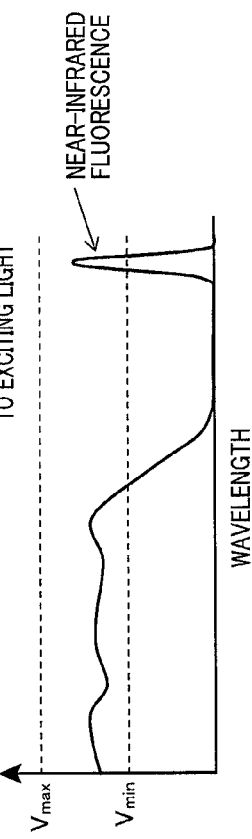

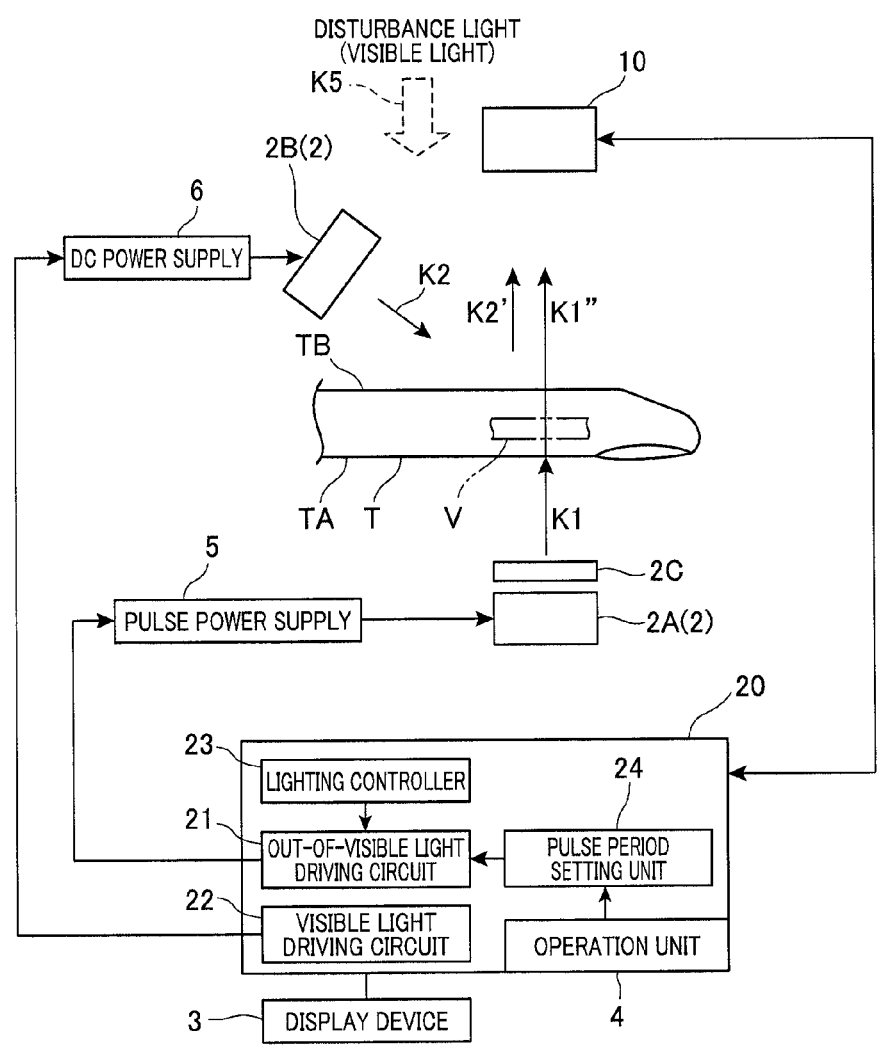

IMAGING SYSTEM

This application is based on Japanese Patent Applications No. 2013-105130 filed on May 17, 2013, which is incorporated by reference in its entirety herein.

FIELD OF THE INVENTION

The present invention relates to an imaging system for outputting a visible light image and an out-of-visible light image while superimposing the out-of-visible light image and the visible light image.

BACKGROUND OF THE INVENTION

At medical sites such as surgical operations, medical diagnosis, etc., a fluorescence image is generated in addition to a normal visible light image by administering fluorescent material such as indocyanine green (ICG) or the like into an affected (diseased) part of a body and imaging the affected part, and both the normal visible light image and the fluorescence image are displayed while superimposing these images to observe the affected part. Here, increase of the light amount of the visible light image causes halation whereas increase of the light amount of the fluorescence image degrades visibility. Therefore, it is necessary to adjust the balance in light amount between the visible light image and the fluorescence image.

Under such circumferences, an imaging system having an optical filter for transmitting visible light and fluorescence therethrough with a desired light-amount balance between the visible light and the fluorescence, and an imaging system having an aperture diaphragm for attenuating(adjusting) visible light are known as an imaging system for generating a visible light image and a fluorescence image (see Japanese Patent No. 4,971,816 and International Publication No. WO2011/007461, for example).

However, the above construction has a problem that the optical system is complicated and the efficiency for light utilization is low because the visible light is attenuated.

SUMMARY OF THE INVENTION

The present invention has been implemented in view of the foregoing situation, and has an object to provide an imaging system that can optimize the balance in light amount between a visible light image and an out-of-visible light image with increase of the efficiency of light utilization.

In order to attain the above object, an imaging system according to the present invention comprises: a first lighting device that irradiates an imaging target object with visible light; a second lighting device that irradiates the imaging target object with out-of-visible light defined as light other than the visible light; an image sensor that photodetects first light caused by the visible light of the first lighting device and coming from the imaging target object, and second light caused by the light of the second lighting device and coming from the imaging target object during a predetermined shutter open period every frame of a predetermined period, and outputs photodetection signals corresponding to photodetection amounts of the first light and the second light; and a controller that generates a visible image based on the photodetection amount of the first light and an out-of-visible image based on the photodetection amount of the second light and outputs a composite image of the visible image and the out-of-visible image, wherein the controller has a lighting controller that turns on the second lighting device with optical power corresponding to the shutter open period in synchronism with the shutter open period.

In the above imaging system, the shutter open period may be adjustable.

In the above imaging system, the lighting controller may turn on the second lighting device with the optical power that substantially equalizes the ratio in intensity between the photodetection signal based on the first light and the photodetection signal based on the second light.

In the above imaging system, the controller may have a user-operable adjusting unit that adjusts the shutter open period. In the above imaging system, the light controller may turn on the second lighting device during the shutter open period only. In the above imaging system, the second light may be fluorescence that is excited by the out-of-visible light from the second lighting device.

The above imaging system may further comprise a pulse power supply that supplies pulsed power (pulsed current) to the second lighting device to turn on the second lighting device in a pulse form (or intermittently). In the above imaging system, the pulsed power may be applied to the second lighting device to turn on the second lighting device during a pulse applying period P while the pulse applying period P is synchronized with the shutter open period.

In the above imaging system, the controller may have a pulse setting unit that is configured to change the pulse applying period P in conformity with change of the shutter open period. In the above imaging system, the pulse applying period P may be set to be within the shutter open period. In the above imaging system, the pulse applying period P may be set at plural times every shutter open period. In the above imaging system, the pulse applying period P may be set once every plural shutter open periods.

According to the present invention, the second lighting device for irradiating the out-of-visible light is turned on with the optical power corresponding to the shutter open period in synchronism with the shutter open period. Therefore, the balance in light amount between the visible image and the out-of-visible image based on the out-of-visible light of the second lighting device can be optimized on the condition that the visible light is not attenuated and the efficiency for light utilization is increased.

BRIEF DESCRIPTION OF THE DRAWINGS

These and other features and advantages of the present invention will become more readily appreciated when considered in connection with the following detailed description and appended drawings, wherein like designations denote like elements in the various views, and wherein:

FIGS. 5A to 5C are diagrams showing the action of an conventional imaging system having an aperture diaphragm, wherein FIG. 5A shows the intensity of incident light to a lens, FIG. 5B shows the transmittance of the aperture diaphragm, and FIG. 5C shows photodetection signals of the imaging system.

FIGS. 6A to 6C are diagrams showing the action of the imaging system when the out-of-visible light source is turned on at all times without adjusting the shutter open period (exposure period), wherein FIG. 6A represents the intensity of incident light to the lens, FIG. 6B represents the transmittance of an exciting light cut filter, and FIG. 6C shows the photodetection signal of the imaging system.

FIGS. 7A to 7D are diagrams showing the action of the imaging system according to the embodiment when the shutter open period (exposure period) is adjusted and the out-of-visible light source is turned on in a pulse lighting fashion, wherein FIG. 7A shows the intensity of incident light to the lens when the out-of-visible light source is turned off, FIG. 7B shows the intensity of incident light to the lens when the out-of-visible light source is turned on, FIG. 7C shows the transmittance of an exciting light cut filter, and FIG. 7D shows the photodetection signal of the imaging system.

FIG. 8 is a diagram showing the construction of an imaging system according to a modification of the present invention.

DETAILED DESCRIPTION OF THE INVENTION

Embodiments according to the present invention will be described hereunder with reference to the drawings.

Figure 9:
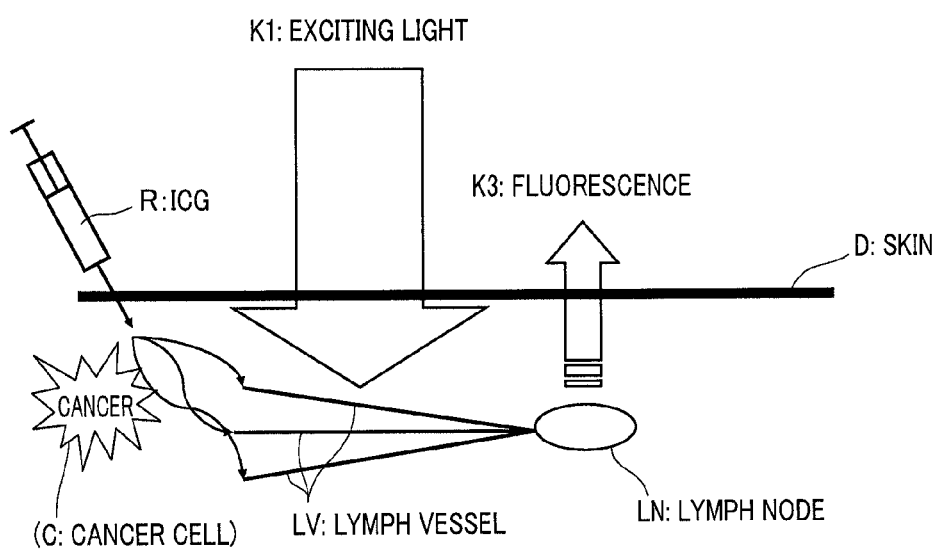
FIG. 9 is a diagram showing a background technique of the present invention.

First, a background technique according to the present invention will be described hereunder in detail with reference to FIG. 9.

A technique of imaging near-infrared reflection light or near-infrared transmission light to generate a near-infrared light absorption image under application of the principle that hemoglobin in blood vessels absorbs near-infrared light is known as a visualization method of visualizing hypodemic blood vessels in medical researches and medical fields.

Furthermore, there is known a technique of administering ICG to lymph vessels, lymph nodes, blood vessels or the like under the skin or in adipose tissues and imaging these tissues to generate near-infrared fluorescence images and visualize these tissues under application of the principle that indocyanine green (ICG) emits near-infrared fluorescence (about 800 to 850 nm) when the indocyanine green (ICG) is irradiated with near-infrared ray (about 740 to 780 nm). For example, when a lymph node LN to which a cancer cell C may metastasize is visualized, fluorescent material R (ICG) is first injected into a subcutaneous tissue. Here, the fluorescent material (ICG) is rapidly absorbed by lymph vessels LV and the lymph node LN. When skin D under which the lymph node LN as an object of interest is located is irradiated with near-infrared exciting light K1 (about 740 to 780 nm), the near-infrared exciting light K1 is transmitted through the subcutaneous tissue by 2 cm, and then reaches the lymph node LN. ICG molecules in the lymph node LN are excited by the near-infrared exciting light K1, and emit near-infrared fluorescence K3 (about 800 to 850 nm). This near-infrared fluorescence K3 is transmitted through the skin D and captured by a camera (not shown).

At medical sites, a region of interest (object of interest) is irradiated with visible light (about 400 to 700 nm) so that a naked-eye work can be optimally performed. Here, the "naked-eye work" is defined as a work which an operator (worker) performs while viewing a working target with his/her naked eye(s).

When a near-infrared absorption image is observed and when a near-infrared fluorescence image is observed, it is desired that a background excluding the region of interest (the near-infrared absorption image or the near-infrared fluorescence image) is imaged with the optimum balance. This is because position information of the region of interest cannot be obtained unless the background is imaged simultaneously with the region of interest.

When the region of interest and the background are imaged with optimum balance by using an imaging system comprising a single image sensor, it is improper to vary the lighting intensity of visible light (the intensity of visible light for illumination). This is because the lighting intensity of visible light should be optimized for the naked-eye work and it should not be changed. When the lighting intensity of visible light is set to be optimum for the naked-eye work, the incident light amount of visible light which is reflected from a subject and incident to the image sensor is frequently excessively large.

Therefore, the background art documents (the specifications of Japanese Patent No. 4,971,816 and International Publication WO 2011/007461) have disclosed a technique of attenuating visible light incident from a subject to an imaging system by an optical filter or an aperture diaphragm.

Since a near-infrared absorption image or a near-infrared fluorescence image is generally faint in intensity, it is difficult to image the region of interest and the background with optimum balance by using the imaging system comprising the single image sensor without executing the technique disclosed in the foregoing background documents under visible-light illumination optimized for the naked-eye work. This is because an excessively large amount of visible light as the background is incident to the image sensor and thus so-called "halation phenomenon", "saturation phenomenon", "smear" or the like occurs.

In a reflection type imaging system for irradiating an imaging target such as fingers, four limbs or the like with near-infrared light and imaging near-infrared reflection light with a single image sensor, or in a transmission type imaging system for irradiating an imaging target such as fingers, four limbs or the like with near-infrared light and imaging near-infrared transmission light with a single image sensor, an optical filter for dimming visible light reflected from the surface of skin under visible-light illumination is inserted in an incident light path of the image sensor. In this case, a predetermined optical filter which optimizes the dimming amount of visible light must be prepared in advance.

When an aperture diaphragm is disposed in place of the optical filter, only the light amount of visible light can be independently and continuously controlled, but the imaging system having the aperture diaphragm is large in size and high in cost.

Therefore, in this embodiment, the light amount balance between the visible light image and the out-of-visible light image can be optimized under the condition that the size of the imaging system is suppressed from increasing and also the efficiency for light utilization is increased.

The imaging system according to this embodiment will be described hereunder in detail.

Figure 1:
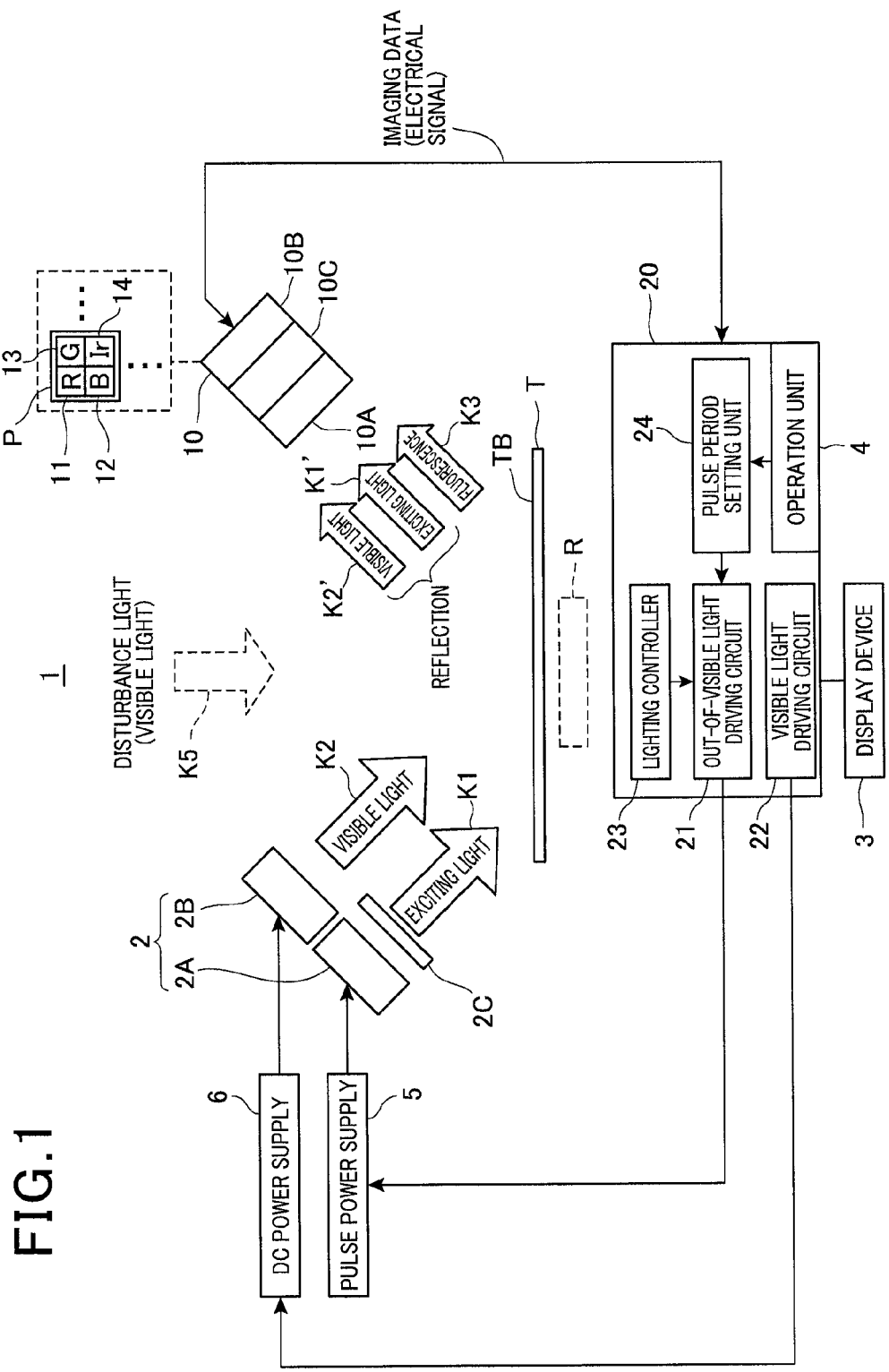
FIG. 1 is a diagram showing an imaging system according to an embodiment of the present invention.

FIG. 1 is a diagram showing the construction of the imaging system according to this embodiment.

The imaging system 1 is a system for generating and displaying a composite color image containing both an out-of-visible light image (fluorescence image) and a visible light image (background image) of an affected (diseased) part (imaging target object) T to which fluorescent material R is administered. This system is configured to have a light source device (light source means) 2, a camera 10, a controller 20 and a display device 3.

The light source device 2 is a device for irradiating the affected part T with exciting light (light other than visible light; hereinafter referred to as "out-of-visible light") K1 for exciting the fluorescent material R and visible light K2 for a background. This device has an out-of-visible light source (second irradiation device) 2A for applying the exciting light K1 and a visible light source (first irradiating device) 2B for applying the visible light K2. The out-of-visible light source 2A and the visible light source 2B are arranged at the imaging target surface TB side of the affected part T.

Here, in this embodiment, ICG (indocyanine green) which is excited by near-infrared light of about 740 to 780 nm in wavelength to emit near-infrared fluorescence of 800 to 850 nm in wavelength is used as the fluorescent material R. Accordingly, a light source for emitting near-infrared light of about 740 to 780 nm in wavelength, for example, an near-infrared LED is used for the out-of-visible light source 2A, and also a non-near-infrared light cut filter 2C for cutting off light of 700 nm or less in wavelength (non-near-infrared light) is provided. Furthermore, for example, a white color LED is used for the visible light source 2B. The visible light source 2B is used to irradiate the imaging target surface TB with visible light K2 for the background. The imaging system as described above may be set up under such a condition that it is exposed to visible light K5 as disturbance light (environmental light) such as light from an indoor light source, for example, a room lamp, monitors, an astral lamp or the like. The imaging system may be set up under a condition that the disturbance light does not exit.

The camera 10 has a lens 10A and a CCD (Charge Coupled Device) image sensor 10B having photodetecting elements arranged discretely in the two-dimensional space, and is disposed at the imaging target face TB side of the affected part T. The camera 10 successively picks up a color image at a predetermined frame rate with predetermined resolution, and successively outputs the pick-up color images as frame-based imaging data to a controller 20. The camera 10 is provided with an exciting light cut filter 10C for cutting off light in a wavelength range (700 to 800 nm in wavelength) which corresponds to exciting light K1' caused by reflection of the exciting light K1 from the imaging target face TB. The exciting light cut filter 10C transmits the fluorescence K3 emitted from the fluorescent material R and the visible light K2' as reflection light of both the visible light K2 and the visible light K5 with transmittance of 100%. Accordingly, only the fluorescence K3 and the visible light K2' can be imaged and displayed as a composite color image without being affected by the exciting light K1 of the out-of-visible light source 2A.

The image sensor 10B is sensitive to both the wavelength range of the fluorescence K3 (the near-infrared wavelength range in this embodiment) and the wavelength range of the visible light K2 and K5. The image sensor 10B has pixels P each of which has photodetecting elements 11 to 14 for photodetecting red light (R), green light (G), blue light (B) and infrared light (Ir), respectively. The photodetecting elements 11 to 13 of red (R), green (G) and blue (B) are sensitive to the wavelengths of the visible light K2', and each of the photodetecting elements 11 to 13 outputs a photodetection signal corresponding to a photodetection amount (the amount of light detected by each photodetecting element) to the controller 20. The photodetecting element 14 for detecting infrared light (Ir) is sensitive to the wavelength range of the fluorescence K3 (that is, near-infrared fluorescence in the neighborhood of the wavelength of 830 nm), and outputs a photodetection signal corresponding to the photodetection amount of the fluorescence K3.

The controller 20 generates a color composite image containing a fluorescence image and a visible light image on the basis of the imaging data of the camera 10 and displays the composite color image on a display device 3. Here, the visible light image is generated on the basis of the photodetection signals from the photodetecting elements 11 to 13 for red, green and blue colors, and the fluorescence image is generated on the basis of the photodetection signals from the photodetecting elements 14 for Ir. The composite color image is equivalent to an image obtained by adding the visible light image and the fluorescence image).

Accordingly, the composite color image described above is displayed such that a fluorescent site obtained by the fluorescence image is superimposed on the visible light image (background image) which is equivalent to a visible image obtained by viewing the affected part T with naked eyes. Therefore, it is unnecessary to observe the affected part T while visually matching the visible light image and the fluorescence image which are displayed separately from each other, and the affected part T can be easily and accurately observed. Particularly, when ICG is used as the fluorescent material P., lymph nodes or bloodstreams in blood vessels are displayed while superimposed on the background(the visible light image), whereby the bloodstreams can be identified at a glance and the correlation between the bloodstreams and surrounding tissues can be clearly comprehended.

Furthermore, the controller 20 has an out-of-visible light driving circuit 21 for driving the out-of-visible light source 2A and a visible light driving circuit 22 for driving the visible light source 2B.

Figure 2:
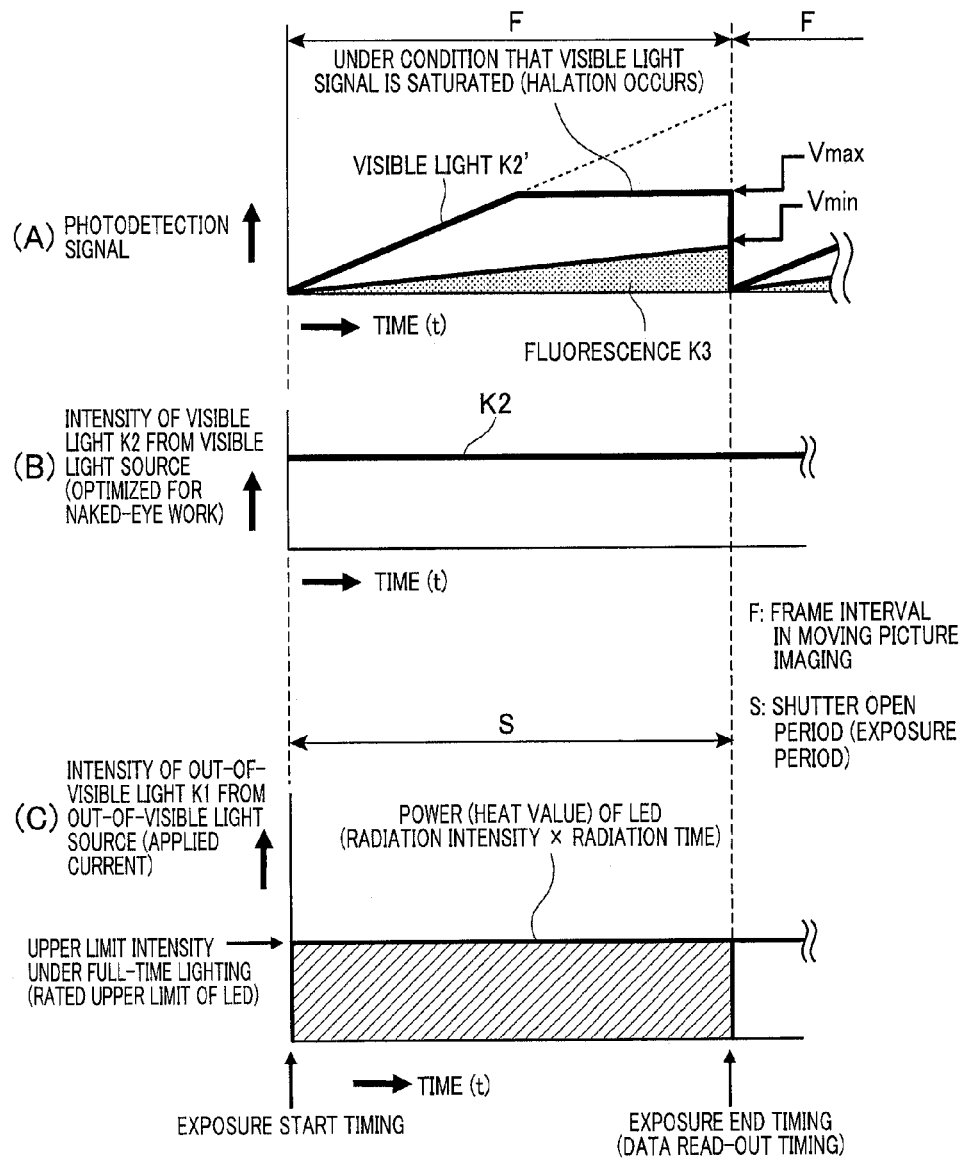
FIG. 2 is a diagram showing a frame of imaging date before a shutter open period (exposure period) is adjusted, wherein (A) represents photodetection signals (photodetection amounts) of visible light and fluorescence in the imaging data, (B) represents the intensity (light amount) of a visible light source, and (C) represents the intensity (light amount) of an out-of-visible light source.

FIG. 2 is a diagram showing imaging data of each frame before a shutter open period (exposure period) S is adjusted. Here, the shutter open period S is defined as a period for which the shutter of the camera 10 is opened to accumulate electrical charges corresponding to the light amount of incident light to the camera 10. Accordingly, the electrical charges accumulated for the shutter open period S corresponds to a photodetection signal from each photodetecting element.

In FIG. 2, (A) represents photodetection signals (photodetection amounts) of visible light and fluorescence in the imaging data of each frame, (B) represents the intensity (light amount) of the visible light K2 from the visible light source 2B, and (C) represents the intensity (light amount) of the out-of-visible light K1 from the out-of-visible light source 2A.

Figure 3:
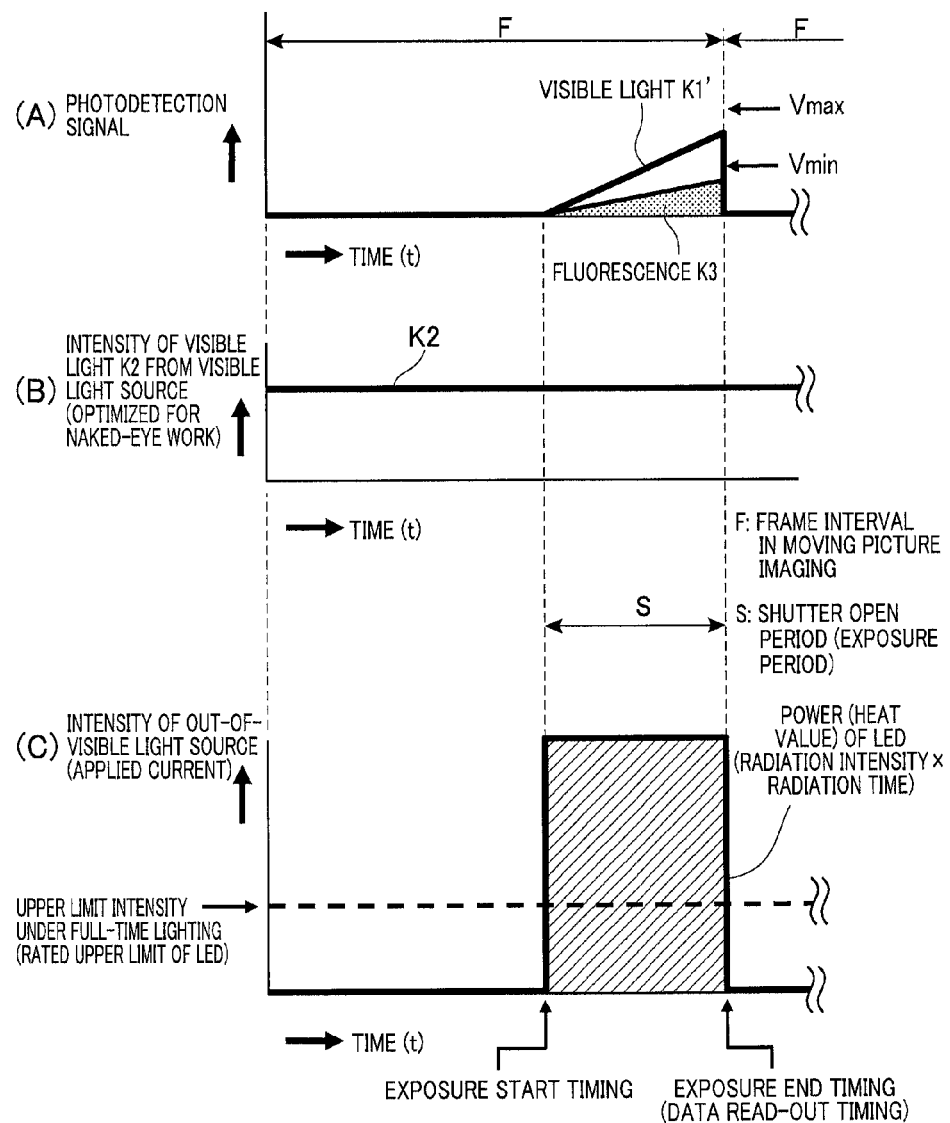
FIG. 3 is a diagram showing a frame of imaging data after the shutter open period (exposure period) is adjusted so that the photodetection amount of the visible light is not more than the maximum amount Vmax, wherein (A) represents photodetection signals (photodetection amounts)of visible light and fluorescence in the imaging data, (B) represents the intensity (light amount) of the visible light source, and (C) represents the intensity (light amount) of the out-of-visible light source.

Furthermore, FIG. 3 is a diagram showing the imaging data of one frame when the shutter open period S is adjusted so that the photodetection amount of the visible light is not more than the maximum value Vmax above which halation occurs. In FIG. 3, (A) represents the photodetection signals (photodetection amounts) of the visible light and the fluorescence in the imaging data of one frame, (B) represents the intensity (light amount) of the visible light K2 from the visible light source 2B, and (C) represents the intensity (light amount) of the out-of-visible light K1 from the out-of-visible light source 2A. In FIGS. 2 and 3, the abscissa axis represents the time t.

The imaging operation of the imaging system 1 is performed according to the "moving picture (video)" imaging manner. Therefore, as shown in (A) of FIG. 2, the maximum length of the shutter open period (exposure period) S is allowed to be set to the length of one frame (frame interval F), for example, 1/30 seconds. Here, in FIGS. 2 to 4, F represents a time period corresponding to one frame of a composite color image. In this embodiment, the end timing of the shutter open period S (shutter closing timing) is set to be coincident with the end of each frame.

The camera 10 shown in FIG. 1 is configured to detect visible light and fluorescence from the affected part T and convert the detected visible light and fluorescence to electrical charges during an adjustable shutter open period S while accumulating the converted electrical charges. Accordingly, as shown in (A) of FIG. 2, the photodetection amounts of the visible light and the fluorescence (the intensities of photodetection signals) which are photodetected by the camera 10 increase during only the shutter open period S. Here, when the photodetection amount of the visible light (the visible light signal) exceeds a predetermined maximum value Vmax and is saturated during the predetermined shutter open period S, halation occurs in a composite color image. Therefore, the finally obtained color image becomes visually unclear. Furthermore, since the light amount of the visible light K2 is optimized to a predetermined value for the naked-eye work, it is difficult to control the light amount of the visible light K2 itself.

Therefore, according to this embodiment, the shutter open period S is adjusted so that the photodetection amount of the visible light K2' does not exceed the maximum value Vmax and thus no halation occurs without adjusting the light amount of the visible light K2. For this purpose, the controller 20 is provided with a user-operable (or externally-operable) operation unit (adjusting means) 4 for adjusting the shutter open period S (FIG. 2) as shown in FIG. 1. The operation unit 4 may be provided in the controller 20 or may be provided as a separate unit out of the controller 20.

When the photodetection amount of the visible light K2' exceeds the maximum value Vmax at or below no halation occurs in the color image as shown in the example of FIG. 2, the controller 20 displays an indication such as a message representing this excess of the photodetection amount of the visible light K2' on the display device 3. The overrun of the photodetection amount of the visible light K2' may be informed in any way. For example, in place of display of the message or the like on the display device 3, a lamp may be turned on/off or an alarm sound may be output from a speaker. Upon reception of this indication or the like, a user operates the operation unit 4 to shorten the shutter open period 5, whereby the shutter open period S can be adjusted so that the photodetection amount of the visible light K2' is not more than the maximum value Vmax.

In this embodiment, the end timing of the shutter open period S is set to be coincident with the end of each frame. Therefore, in order to adjust the shutter open period S, the start timing of the shutter open period S (exposure start timing) is adjusted. Accordingly, by adjusting the start timing of the shutter open period S, the photodetection amount of the visible light K2' can be set to be equal to or less than the maximum value Vmax as shown in (A) of FIG. 3, and occurrence of halation can be prevented.

As not shown, when the photodetection signal (photodetection amount) of the visible light K2' in the imaging data is less than the maximum value Vmax during the shutter open period S, it is unnecessary to adjust the shutter open period S. However, when the photodetection signal (photodetection amount) of the visible light K2' is insufficient, the shutter open period S may be lengthened within the range of the frame interval F so that the photodetection signal (photodetection amount) of the visible light K2' is equal or closer to the maximum amount Vmax. The controller 20 may control the display device 3 so that the photodetection amount of the visible light K2' is displayed on the display device 3. The photodetection amount of the visible light K2' may be automatically or manually displayed on the display device 3 on a real-time basis or intermittently, for example.

Here, the camera 10 shown in FIG. 1 has characteristics that the sensitivity to the near-infrared region is lower than the sensitivity to the visible region. When ICG is used as the fluorescent material R, the rate of the light amount of the fluorescence K3 to that of the irradiated exciting light K1 is equal to about 1%. Accordingly, as shown in (A) of FIG. 3, the photodetection amount of the fluorescence K3 is smaller than that of the visible light K2'. When the photodetection amount of the fluorescence K3 for a predetermined shutter open period S is less than a predetermined minimum value Vmin, visibility of a near-infrared fluorescence image in a composite color image cannot be secured.

Therefore, according to this embodiment, in order to secure the visibility of a fluorescence image in a composite color image, the controller 20 is provided with a lighting controller (lighting control means) 23 for turning on the out-of-visible light source 2A with optical power which enables the photodetection amount of the fluorescence K3 to be equal to or more than the minimum amount Vmin at or above the visibility can be secured. Accordingly, the optical power of the out-of-visible light source 2A is adjusted by the lighting controller 23 so that the photodetection amount of the fluorescence K3 is not less than the minimum amount Vmin as shown in (A) of FIG. 4, whereby the image condition (state) of a fluorescent site in the composite color image of the affected part T can be adjusted simply on a real-time basis.

Particularly, the indoor light source (the indoor lamp or the like) which induces disturbance light is configured to irradiate the visible light K5 with which the naked-eye work can be performed. Therefore, it is frequently impossible to control the intensity and irradiation time of the visible light K5. According to this embodiment, the optical power of the out-of-visible light source 2A is adjusted in accordance with the optical power (intensities) of both the disturbance light K5 and the visible light K2 of the visible light source 2B under the condition that the indoor light source is turned on as usual, whereby the balance in light amount between the visible image (background image) and the out-of-visible light image (fluorescence image) can be optimized.

Here, the ratio between the photodetection amount (V1) of the visible light (reflection light K2') and the photodetection amount (V2) of the fluorescence K3 under the condition that the balance between the visible light K2' and the fluorescence K3 is optimized is represented by R(V1:

V2). In this case, the lighting controller 23 of this embodiment is configured to turn on the out-of-visible light source 2A with adjustable optical power which substantially equalizes the ratio of the photodetection amounts of the visible light K2' and the fluorescence K3 to R(V1:V2). The optimum ratio R(V1:V2) may be preset in a memory device (not shown) provided to the lighting controller 23 or arbitrarily set by a user.

Accordingly, the composite color image (moving picture) based on the optimum visible light and the optimal fluorescence can be easily obtained by optimizing the balance in light amount between the light components (the visible light K2' and the fluorescence K3) incident to the photodetecting elements 11 to 14 (R(V1:V2)) (FIG. 1) and then setting the shutter open period S for the photodetecting elements 11 to 14 to a possible longest value. Furthermore, even when the photodetection amount of the visible light K2' underruns Vmax because the shutter open period S is adjusted after the balance between the photodetection amounts of the visible light K2' and the fluorescence K3 is optimized to R(V1:V2), the imaging system of this embodiment can be kept to the state that the balance in light amount between the visible light image (background image) and the out-of-visible image (fluorescence image) is optimized.

Here, permissible maximum power is defined for LEDs used for the out-of-visible light source 2A. Accordingly, when the optical power of each LED used for the out-of-visible light source 2A is increased under the state that the out-of-visible light source 2A is turned on at all times (under full-time lighting), there is a risk that the optical power of each LED reaches the permissible maximum power or more.

Accordingly, when the out-of-visible light source 2A (FIG. 1) is turned on at all times, the upper limit of the heat value of LEDs used for the out-of-visible light source 2A is determined to a predetermined limit value (radiation intensity×irradiation time) in consideration of a rated upper limit under continuous current application or a safety upper limit of irradiation to the imaging target. Therefore, the light amount of the fluorescence K3 induced by the out-of-visible light (exciting light) K1 is remarkably smaller than the light amount of the reflection visible light K2' caused by the irradiated visible light K2 and KS. Accordingly, it is considered that the number of LEDs used for the out-of-visible light source 2A is increased to suppress the optical power (heat value) of each LED. However, the increase in number of the LEDs causes increase in whole size of the out-of-visible light source 2A and in cost.

As described above, when the shutter open period S is set to 1/30 second (the longest period) to sufficiently photodetect the faint fluorescence K3, the photodetection signal of the visible light K2' reaches a saturation level at which halation occurs in a color image (FIG. 2), and the composite color image becomes unclear.

Therefore, the controller 20 of this embodiment is configured to turn on the out-of-visible light source 2A (keep the out-of-visible light source 2A to ON-state) during only the shutter open period S and turn off the out-of-visible light source 2A (keep the out-of-visible light source 2A to OFF-state) during the other period (i.e., the shutter closing period) as shown in (C) of FIG. 3.

Figure 4:
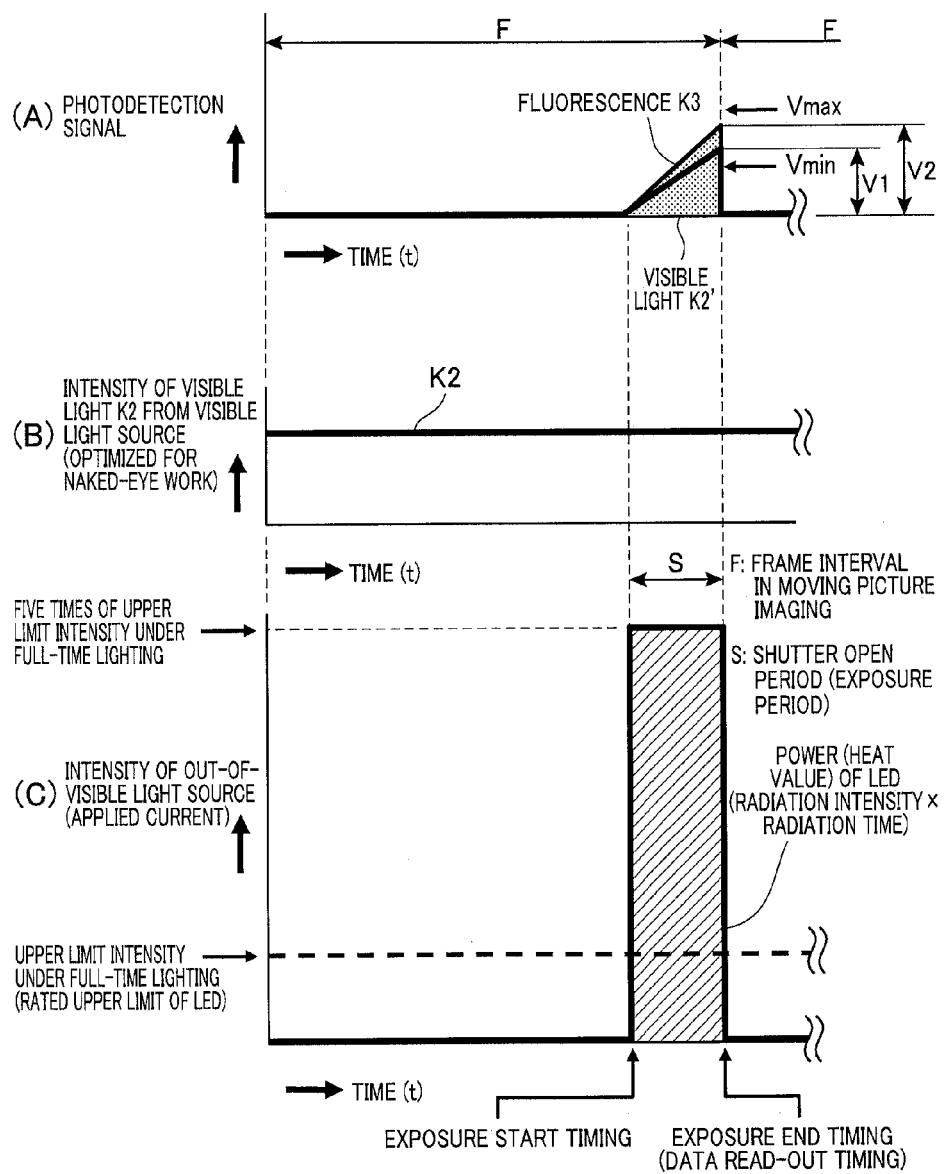
FIG. 4 is a diagram showing a frame of imaging data when the out-of-visible light source 2A is turned on with such optical power (optical output) that the photodetection amount of the fluorescence is not less than the minimum amount Vmin, wherein (A) represents the photodetection signals (photodetection amounts) of visible light and fluorescence in imaging data, (B) represents the intensity (light amount) of the visible light source and (C) represents the intensity (light amount) of the out-of-visible light source.

Specifically, as shown in FIG. 1, the out-of-visible light driving circuit 21 is connected to the out-of-visible light source 2A through a pulse power supply 5 for supplying pulsed power (current) to the out-of-visible light source 2A at a predetermined period Tp. Here, the out-of-visible light driving circuit 21 drives the pulse power supply 5 to supply pulsed power to the out-of-visible light source 2A during a pulse applying period P in synchronism with the shutter open period S every predetermined period Tp. That is, the pulsed power (current) is applied to the out-of-visible light source 2A during the pulse applying period P corresponding to the shutter open period S every predetermined period Tp, whereby the out-of-visible light source 2A is turned on (i.e., the out-of-visible light K1 is irradiated) during only the shutter open period S. The predetermined period Tp is set in synchronism with the shutter ON/OFF period of the camera 10 as shown in FIGS. 3 and 4. These periods may be set in synchronism with the frame rate, or arbitrarily set irrelevantly to the frame rate.

Specifically, the out-of-visible light driving circuit 21 operates the pulse power supply 5 so that the pulse rising timing of the pulsed power (that is, the ON-timing of the out-of-visible light source 2A) is coincident with the shutter open timing of the shutter open period S and also the pulse falling timing of the pulsed power (that is, the OFF-timing of the out-of-visible light source 2A) is coincident with the shutter close timing (that is, the end of each frame) as shown in (C) of FIGS. 3 and 4.

Furthermore, the controller 20 is provided with a pulse period setting unit 24, and the pulse period setting unit 24 adjusts the pulse period Tp of the pulse power supply 5 in accordance with an adjusted shutter open period S and outputs the adjusted pulse period Tp to the out-of-visible light driving circuit 21 every time the shutter open period S is adjusted by the operation of the operation unit 4. Specifically, the pulse applying period P (the pulse rising and falling timings) of the predetermined period Tp of the pulse power supply 5 is adjusted to be coincident with the adjusted shutter open period S by the pulse period setting unit 24 every time the shutter open period S is adjusted by the operation of the operation unit 4.

As described above, the lighting controller 23 of the controller 20 controls the out-of-visible light driving circuit 21 to turn on the out-of-visible light source 2A during only the shutter open period S at the predetermined period Tp while the turn-on start timing of the out-of-visible light source 2A is coincident with the shutter open timing of the shutter open period S (i.e., the exposure start timing) and the turn-off start timing of the out-of-visible light source 2A is coincident with the shutter close timing of the shutter open period S (i.e., the exposure end timing, the data read-out timing) and further coincident with the end timing of the frame interval F.

In this case, the upper limit of the heat value (J: Jule) of LEDs used for the out-of-visible light source 2A which is defined by W×S (radiation intensity (W: Watt)×irradiation time (S: Second)) is also set to the same value as the case where the out-of-visible light source 2A is turned on at all times (represented by the areas of the hatched portions in FIGS. 2, 3 and 4). Accordingly, the optical power of the out-of-visible light source 2A can be increased while the optical power of each LED used for the out-of-visible light source 2A is prevented from reaching the permissible maximum power and also the size of the out-of-visible light source 2A is prevented from increasing.

Here, the rate of the turn-on time (shutter open period S) of the out-of-visible light source 2A to the frame interval F (1/30 second) is defined as the duty ratio of the out-of-visible light source 2A. In this embodiment, LEDs are used for the out-of-visible light source 2A (FIG. 4). Therefore, when the duty ratio of the out-of-visible light source 2A is set to 20% (1/150 second), the maximum current to be applicable to LEDs is increased five times, so that the radiation intensity of the out-of-visible light source 2A is five times as high as the upper limit of the radiation intensity when the out-of-visible light source 2A is turned on at all times (i.e., under full-time lighting).

As described above, according to this embodiment, the irradiation of the exciting light is performed during only the shutter opening period S by applying the principle that the amount of light incident to each of the photodetecting elements 11 to 14 (FIG. 1) within the shutter open period S is integrated and converted to the photodetection signal, whereby the relatively strong effect of visible light is attenuated and the balance in light amount between the visible light image and the fluorescence image can be optimized.

The visible light driving circuit 22 is connected to the visible light source 2B through the DC power supply 6 for supplying power to the visible light source 2B at all times, and the controller 20 controls the visible light driving circuit 22 to turn on the visible light source 2B at all times. The visible light driving circuit 22 may be connected to a pulse power source as in the case of the out-of-visible light driving circuit 21 to turn on the visible light source 2B for only the shutter open period S.

In the above embodiment, the lighting controller 23 controls the out-of-visible driving circuit 21 to turn on the out-of-visible light source 2A in synchronism with the shutter open period S so that the pulse applying period P of the pulsed power is coincident with the shutter open period S. However, the pulse applying period P of the pulsed power is not necessarily coincident with the shutter open period S. For example, the pulse applying period P of the pulsed power may be set to be within the shutter open period S, cover the shutter open period S or be displaced from the shutter open period S under the condition that any overlap period exists between the pulse applying period P and the shutter open period S. In this case, it is also needless to say that these periods S and P are set so that no halation occurs and the visibility can be secured.

Furthermore, in the above embodiment, the pulse applying period P and the shutter opening period S are set in one-to-one correspondence in each frame interval F. However, these periods P and S are not necessarily set in one-to-one correspondence. For example, plural pulse applying periods P may be set within each shutter open period S or a pulse applying period P may be set every plural shutter open periods S. This setting of these periods P and S may be applied to a stroboscopic imaging system or the like, for example.

A conventional imaging system having an aperture diaphragm, an imaging system in which the shutter open period (exposure term) is not adjusted and the out-of-visible light source 2A is turned on at all times (under full-time lighting) and the imaging system 1 of this embodiment in which the shutter open period S is adjusted and the out-of-visible light source 2A is turned on in a pulse form will be described with reference to FIGS. 5 to 7 while comparing these image systems.

Figure 5A:
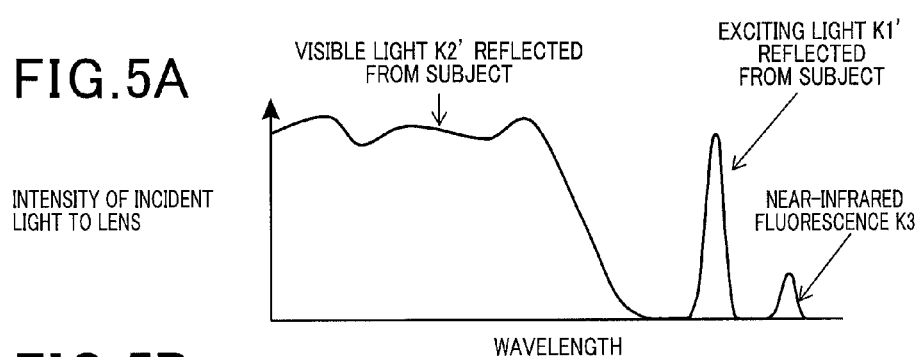
Figure 5B:
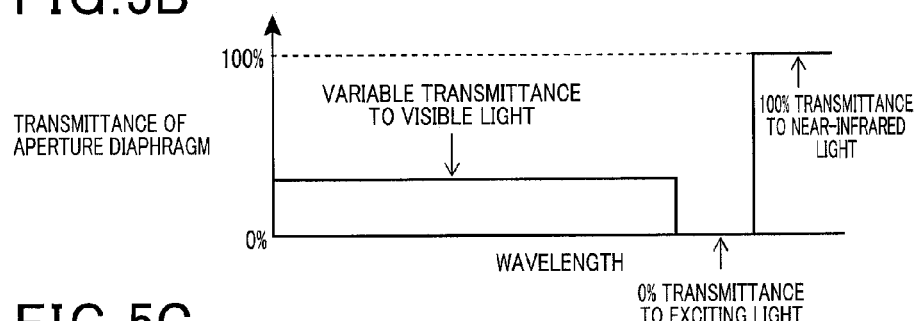
Figure 5C:
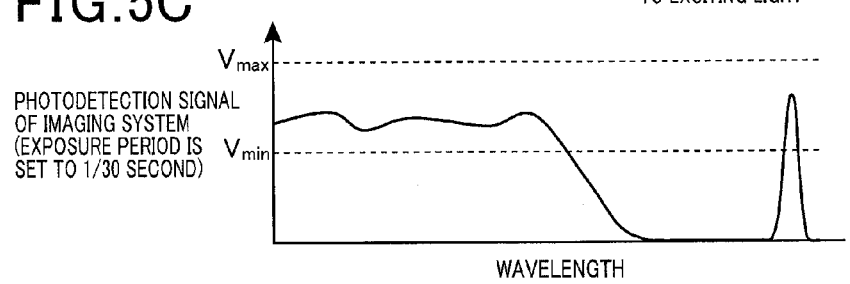

FIGS. 5A to 5C are diagrams showing the action of the conventional imaging system having the aperture diaphragm, wherein FIG. 5A shows the intensity of incident light to the lens of the camera, FIG. 5B shows the transmittance of the aperture diaphragm and FIG. 5C shows the photodetection signal of the imaging system. In the example of FIGS. 5A to 5C, the out-of-visible light source 2A is turned on at all times, and the shutter open period S (exposure period) is set to 1/30 second.

As shown in FIG. 5A, visible light K2' reflected from a subject (affected part T), exciting light K1' reflected from the subject and near-infrared fluorescence K3 induced by exciting light K1 are incident to the lens. In the conventional imaging system having the aperture diaphragm, the aperture diaphragm is an optical filter that is configured to attenuate the visible light K2' (i.e., transmittance is variable), cut off the exciting light K1' (transmittance is equal to 0%) and transmit the fluorescence K3 (transmittance is equal to 100%), and the transmittance to the visible light K2' is freely variable. That is, the aperture diaphragm can control only the transmittance to visible light, and thus when the fluorescence K3 is faint, the photodetection amount of the fluorescence K3 is very small. Furthermore, this imaging system has a problem that the optical system of the imaging system is complicated because the aperture diaphragm is provided and also the efficiency of light utilization is low because visible light must be attenuated.

Figure 6A:
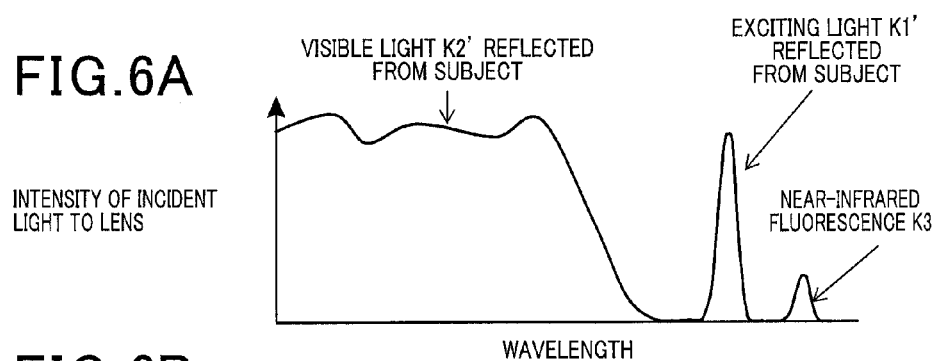
Figure 6B:
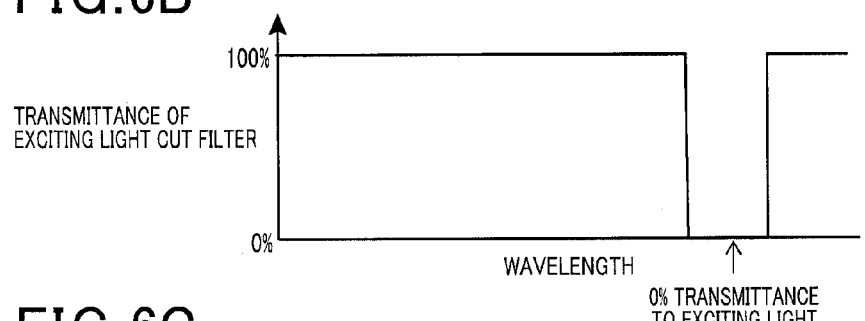
Figure 6C:
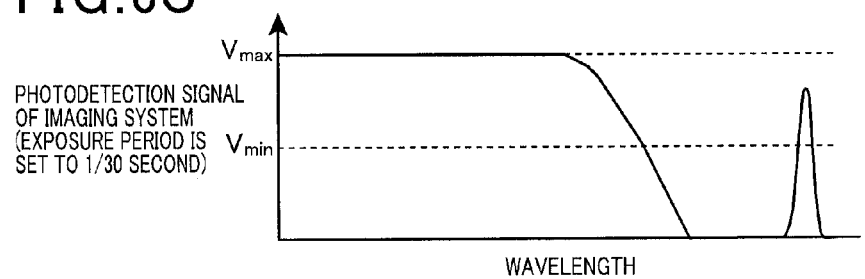

FIGS. 6A to 6C are diagrams showing the action of the imaging system when the shutter open period S (exposure period) is not adjusted and the out-of-visible light source 2A is turned on at all times, wherein FIG. 6A shows the intensity of incident light to the lens of the camera 10, FIG. 6B shows the transmittance of the exciting light cut filter 10C, and FIG. 6C shows the photodetection signal of the imaging system.

In this imaging system, as shown in FIG. 6A, visible light K2', exciting light K1' and near-infrared fluorescence K3 are incident to the lens as in the case of FIG. 5A. In this imaging system, the exciting light cut filter 10C that cuts off the exciting light K1' (transmittance of 0%) and transmits the visible light K2' and the fluorescence K3 (transmittance of 100%) as shown in FIG. 6B is used in place of the aperture diaphragm as in the case of this embodiment. When the exposure period is set to 1/30 to sufficiently photodetect the faint fluorescence K3, the photodetection amount of the visible light K2' (visible light signal) exceeds the maximum amount Vmax and is saturated, so that halation occurs in a composite color image.

FIGS. 7A to 7D are diagrams showing the action of the imaging system 1 of this embodiment in which the shutter open period S (exposure period) is adjusted and the out-of-visible light source 2A is turned on in the pulse form. FIG. 7A shows the intensity of incident light to the lens of the camera 10 when the out-of-visible light source 2A is turned off, FIG. 7B shows the intensity of incident light to the lens when the out-of-visible light source 2A is turned on, FIG. 7C shows the transmittance of the exciting light cut filter and FIG. 7D shows the photodetection signal of the imaging system 1.

In this embodiment, as described above, the shutter open period S is shortened, the out-of-visible light source 2A (FIG. 1) is turned on during only the shutter open period S, and the optical power of the out-of-visible light source 2A is adjusted so that the photodetection amount of the fluorescence K3 (the fluorescence signal) is not less than the minimum value Vmin. Accordingly, occurrence of halation in the composite color image can be prevented, and the light-amount balance between the visible light image and the fluorescence image can be optimized. Specifically, since the duty ratio of the out-of-visible light source 2A is set to 20%, the radiation intensity of the out-of-visible light source 2A can be increased five times as compared with the cases of FIGS. 5A and 6A as shown in FIG. 7B.

As described above, the imaging system of this embodiment is provided with the lighting controller 23 for turning on the out-of-light visible source in synchronism with the shutter open period S so that exciting light for inducing fluorescence from the fluorescent material R is generated with optical power which corresponds to the shutter open period S. According to this construction, the light-amount balance between the visible light image (background image) and the out-of-visible light image (fluorescence image) can be optimized while the efficiency of light utilization is increased without attenuating the visible light. Furthermore, unlike the prior arts, it is unnecessary to provide the aperture diaphragm, so that the imaging system 1 can be designed without increasing the size thereof, and manufactured at low cost.

According to this embodiment, the shutter open period S can be adjusted, and more specifically the operation unit 4 which is operable by a user to adjust the shutter open period S is provided. With this configuration, the shutter open period S can be adjusted so that the photodetection amount of visible light is not more than the maximum amount Vmax at or below no halation occurs, thereby preventing occurrence of halation in a composite color image.

Furthermore, according to this embodiment, the lighting controller 23 is configured to irradiate exciting light with the optical output which substantially equalizes the ratio V1:V2 of the respective intensities of the photodetection signals of the reflection light of the visible light and the fluorescence. With this configuration, the light-amount balance between the visible light image (background image) and the out-of-visible light image (fluorescence image) is kept to be optimum even when the shutter open period S is adjusted.

Still furthermore, according to this embodiment, the lighting controller 23 is configured so that the exposure end timing (imaging data read-out timing) is coincident with the end timing of each frame interval F and the out-of-visible light of the out-of-visible light source 2A is irradiated during only the shutter open period S. With this configuration, the power supplied to the LEDs used for the out-of-visible light source 2A can be prevented from reaching the permissible maximum power of the LEDs, and the out-of-visible light source 2A can be prevented from increasing in size.

The foregoing embodiment is an example of the present invention, and various modifications and alterations may be arbitrarily made without departing from the subject matter of the present invention.

For example, in the above embodiment, the shutter open period S is set to $1/150$ second. However, the shutter open period S is not limited to this value, and it may be set to the frame interval F ($1/30$ second) or less. The shutter open period S is adjusted to optimize the light-amount balance between the visible light image (background image) and the out-of-visible light image (fluorescence image), and it may be set to, for example, $1/30$ second, $1/150$ second, $1/300$ second or $1/1000$ second.

Furthermore, in the above embodiment, the frame interval F is set to $1/30$ second. However, the frame interval F is not limited to this value. In the above embodiment, the end timing of the shutter open period S is coincident with the end of each frame. However, the end timing of the shutter period S is not necessarily required to be coincident with the end of the frame.

In the above embodiment, the image sensor 1013 has the photodetecting elements 11 to 14 for photodetecting red light (R), green light (G), blue light (B) and infrared ray (Ir) respectively which are integrally provided every pixel P to generate a color image (composite image) containing a fluorescence image and a visible light image in a lump. However, the present invention is not limited to this arrangement of the photodetecting elements 11 to 14. For example, the image sensor 10B may have a group unit of photodetecting elements 11 to 13 and a group unit of photodetecting element 14 which are provided separately from each other.

In this case, a visible light image (background image and an out-of-visible image (fluorescence image) are generated separately from each other, and then these images are superimposed to form a composite color image.

Furthermore, in the above embodiment, the visible light K2' caused by reflection of both the visible light K2 and the disturbance light K5 from the imaging target object is photodetected. However, when the visible light of the disturbance light is sufficient to the naked-eye work or the like, the visible light source 23 may be turned off by the controller 20, or the visible light source 2B, the visible light driving circuit 22 and the DC power supply 6 may be omitted. In these cases, the optical power of the out-of-visible light source 2A is adjusted in conformity with the optical power of the visible light of the disturbance light, whereby the light-amount balance between the visible light image (background image) and the out-of-visible light image (fluorescence image) can be optimized. When there is no disturbance light, the visible light source 2B may be turned on while increasing the optical power by the amount corresponding to the disturbance light.

In the above embodiment, the user-operable operation unit 4 for adjusting the shutter open period S is provided. However, in place of the operation unit 4, the controller 20 itself may be configured to automatically or manually set the shutter open period S so that the photodetection amount of the visible light K2' is not more than the maximum amount Vmax at or below which no halation occurs. In this case, it is unnecessary that the indication representing that the photodetection amount of visible light exceeds the maximum value Vmax is displayed on the display device 3.

Furthermore, this embodiment uses ICG as the fluorescent material R. However, the present invention is not limited to this material. When materials other than ICG are used as the fluorescent material R, LEDs capable of exciting these fluorescent materials and emitting exciting light are used for the out-of-visible light source 2A.

The above embodiment uses LEDs as the light sources of the light source device 2. However, the light source may be a light emitting element such as organic EL or the like, a lamp or the like.

In the above embodiment, the imaging system 1 is configured as an imaging system for medical applications in which an affected (disease) part is set as an imaging target object. However, the present invention is not limited to the medical applications, and the imaging system according to this invention may be used as an imaging system for industrial applications in which a part is set as an imaging target object. In this case, apart as an imaging target object is infiltrated with fluorescent material which emits fluorescence upon irradiation of ultraviolet light thereto, and the part is irradiated with ultraviolet light and visible light, whereby a fluorescence image representing any defect such as a crack or the like occurring in the part is output while superimposed on a visible image as a background image, whereby the defect of the part can be visualized.

Furthermore, as disclosed in JP-A-2013-36889, the imaging system may be an imaging system for agriculture in which a plant is set as an imaging target object. In this case, the plant is irradiated with visible light and exciting light for exciting chlorophyll and/or plant pathogen. Accordingly, a fluorescence image caused by the chlorophyll and/or the plant pathogen is output while superimposed on a visible image as a background, and the infection state of the plant can be visualized.

In the above embodiment, the imaging system 1 is configured as a reflection type imaging system for photodetecting visible light reflected from an imaging target object. However, the imaging system may be configured as a transmission type imaging system for photodetecting visible light transmitted through an imaging target object. In this case, the lighting controller 23 may turn on the out-of-visible light source 2A with optical power which can substantially equalize the ratio between the intensities of respective photodetection signals based on visible light transmitted through the imaging target object and fluorescence.

In the above embodiment, the imaging system 1 is configured as a fluorescence type imaging system for photodetecting fluorescence induced by out-of-visible light from the out-of-visible light source 2A. However, the imaging system 1 may be configured as a reflection type imaging system for photodetecting out-of-visible light which is irradiated from the out-of-visible light source 2A and reflected from the imaging target object or a transmission type imaging system for photodetecting out-of-visible light transmitted through the imaging target object.

In the above embodiment, exciting light for exciting fluorescent material is used as the out-of-visible light. However, when fluorescent material is not administered to the imaging target object, the out-of-visible light is not necessarily the exciting light. An imaging system in this case will be described hereunder.

FIG. 8 is a diagram showing an imaging system 100 for photodetecting out-of-visible light transmitted through an imaging target object without administering fluorescent material to the imaging target object. The same parts as the imaging system 1 shown in FIG. 1 are represented by the same reference numerals, and the description thereof is omitted.

In the imaging system 100, a finger T is set as an imaging target object, the dorsal surface of the finger T as anon-imaging target face TA is irradiated with out-of-visible light K1 (for example, infrared ray) from the out-of-visible light source 2A of the light source device 2, and the ventral surface of the finger T as an imaging target face TB is irradiated with visible light K2 from the visible light source 2B of the light source device 2. That is, the out-of-visible light source 2A is disposed at the non-imaging target face TA side, and a camera 10 is disposed at the imaging target face TB side so as to confront the out-of-visible light source 2A through the finger T. Furthermore, the visible light source 2B is disposed at the imaging target face TB side. The out-of-visible light source 2A, the visible light source 23, the non-near-infrared light cut filter 2C and the camera 10 are the same as the imaging system 1 shown in FIG. 1 except for the arrangement positions thereof, and are represented by the same reference numerals as shown in FIG. 1.

The camera 10 photodetects transmitted light K1" of the out-of-visible light K1 and visible light K2' which is caused by reflection of visible light K2 of the visible light source 2B and visible light K5 of disturbance light from the imaging target face TB of the finger T, and outputs the photodetection result as imaging data to the controller 20. The controller 20 generates an out-of-visible light (infrared light) image and a visible light image on the basis of the imaging data of the camera 10 and displays a color image as a composite image of the out-of-visible light image and the visible light image on the display device 3.

In this composite color image, an infrared site (for example, a blood vessel V of the finger T) is displayed while superimposed on the same visible image as viewed when the finger T is observed with the naked eye(s). In the example of FIG. 8, the lighting controller 23 may turn on the out-of-visible light source 2A with optical power which substantially equalizes the ratio in intensity between the photodetection signals of the visible light K2' reflected from the finger T and the transmitted light K1" transmitted through the finger T. In the example of FIG. 8, the optical power of the out-of-visible light source 2A is also adjusted in conformity with the optical power of both the disturbance light and the visible light from the visible light source 2B under the condition that the indoor light source is turned on as usual as in the case of the imaging system shown in FIG. 1, whereby the balance in light amount between the visible light image and the out-of-visible light image can be optimized. Furthermore, in the example of FIG. 8, when the visible light of the disturbance light is sufficient, the controller 20 may turn off the visible light source 2B, or the visible light source 2B, the visible light driving circuit 22 and the DC power supply 6 may be omitted.

The invention claimed is:

1. An imaging system comprising:
a first lighting device that irradiates an imaging target object with visible light;
a second lighting device that irradiates the imaging target object with out-of-visible light defined as light other than the visible light;
an image sensor that photodetects first light caused by the visible light of the first lighting device, which comes from the imaging target object, and second light caused by the out-of-visible light of the second lighting device, which comes from the imaging target object during a predetermined shutter open period every frame of a predetermined period, and outputs photodetection signals corresponding to a photodetection amount of the first light and a photodetection amount of the second light; and
a controller that generates a visible image based on the photodetection amount of the first light and an out-of-visible image based on the photodetection amount of the second light and outputs a composite image of the visible image and the out-of-visible image, wherein
the controller comprises:
a visible light driving circuit that turns on the first lighting device with a first optical power;
an out-of-visible light driving circuit that turns on the second lighting device with a second optical power in synchronism with the shutter open period;
a lighting controller that adjusts the second optical power in view of a ratio between the photodetection amount of the first light and the photodetection amount of the second light;
wherein one or a plurality of the shutter open period is set every frame,
the lighting controller adjusts the second optical power of the second lighting device in such a manner that a ratio V1:V2 is kept at an optimum ratio while maintaining the first optical power of the first lighting device, where V1 represents the photodetection amount of the first light corresponding to the shutter open period and V2 represents the photodetection amount of the second light corresponding to the shutter open period; and
the out-of-visible light driving circuit turns on the second lighting device only during the shutter open period and turns off the second lighting device during other than the shutter open period.

2. The imaging system according to claim 1, wherein the shutter open period is adjustable.

3. The imaging system according to claim 1, wherein the lighting controller turns on the second lighting device with the optical power that substantially equalizes the ratio in intensity between the photodetection signal based on the first light and the photodetection signal based on the second light.

4. The imaging system according to claim 2, wherein the controller has a user-operable adjusting unit that adjusts the shutter open period.

5. The imaging system according to claim 1, wherein the second light is fluorescence that is induced by the out-of-visible light from the second lighting device.

6. The imaging system according to claim 1, further comprising a pulse power supply that supplies pulsed power to the second lighting device to turn on the second lighting device in a pulse form.

7. The imaging system according to claim 6, wherein the pulsed power is applied to the second lighting device to turn on the second lighting device during a pulse applying period P that is synchronized with the shutter open period.

8. The imaging system according to claim 7, wherein the controller has a pulse setting unit that is configured to change the pulse applying period P in conformity with change of the shutter open period.

9. The imaging system according to claim 8, wherein the pulse applying period P is set to be within the shutter open period.

10. The imaging system according to claim 7, wherein the pulse applying period P is set at plural times every shutter open period.

11. The imaging system according to claim 7, wherein the pulse applying period P is set once every plural shutter open periods.

12. The imaging system according to claim 1, wherein the lighting controller turns on the second lighting device coincident with the start timing of the shutter open period and drives the second lighting device continuously during the shutter open period, and turns off the second lighting device coincident with end timing of the shutter open period.

13. the imagining system according to claim 5, further comprising an exciting light cut filter cutting off exciting light that induces the fluorescence and is directed toward the imaging sensor.

* * * * *